US005626621A

United States Patent [19]
Skoglund et al.

[11] Patent Number: 5,626,621
[45] Date of Patent: May 6, 1997

[54] DUAL CHAMBER, MULTI-MODE EXTERNAL PACEMAKER

[75] Inventors: Richard A. Skoglund, Maple Grove; Carl D. Schmuland, Lino Lakes; Robert A. Colbert, Minneapolis, all of Minn.

[73] Assignee: Medtronic, Inc., Minneapolis, Minn.

[21] Appl. No.: 554,877

[22] Filed: Nov. 7, 1995

[51] Int. Cl.$^6$ ................................................ A61N 1/368
[52] U.S. Cl. ................................................ 607/10; 607/9
[58] Field of Search ................................... 607/10, 9, 30

[56] References Cited

U.S. PATENT DOCUMENTS

| | | | |
|---|---|---|---|
| 3,717,153 | 2/1973 | Bowers | 128/419 P |
| 4,248,238 | 2/1981 | Joseph | 607/9 |
| 4,284,082 | 8/1981 | Funke et al. | 607/9 |
| 4,401,119 | 8/1983 | Herpers | 128/419 PG |
| 4,407,287 | 10/1983 | Herpers | 28/419 PG |
| 4,476,869 | 10/1984 | Bihn | 128/419 PT |
| 4,553,547 | 11/1985 | Keimel | 607/30 |
| 4,585,006 | 4/1986 | Livingston et al. | 607/10 |
| 5,172,691 | 12/1992 | Gahnberg et al. | 128/419 PG |
| 5,231,985 | 8/1993 | Sutton et al. | 607/18 |
| 5,304,209 | 4/1994 | Adams et al. | 607/30 |

OTHER PUBLICATIONS

"External A–V Sequential Demand Pacemaker Model 5330" Medtronic publication MC871136–70 UC8901874EN, Apr. 1986 ©1986, Medtronic, Inc.
"Medtronic® Model 5342 Temporary Pacemaker", UC9101417EN Copyright© 1991 by Medtronic, Inc.
MODEL 5345 Temporary Pacemaker, "Competitive Comparison to Pace Medical's Model 4553 Micro–Pace (Siemens–Pacesetter Model 3070)" UC9203901EN ©Medtronic, Inc. 1993.
"Medtronic Dual C hamber Temporary Pulse Generator Model 5345—Quick Operation List" UC8904312aEN ©Medtronic, Inc. 1991.

"Medtronic® DDD Temporary Pacemakers", UC9000091aEN, © by Medtronic, Inc.
"Model 5345 Temporary Pacemaker", UC9002600aEN, © Medtronic, Inc. 1991.

(List continued on next page.)

*Primary Examiner*—William E. Kamm
*Assistant Examiner*—Kennedy J. Schaetzle
*Attorney, Agent, or Firm*—Thomas F. Woods; Reed A. Duthler; Harold R. Patton

[57] ABSTRACT

One embodiment of the present invention is a mode switching method and apparatus for an external, dual chamber cardiac pacemaker having multiple single chamber and dual chamber primary pacing modes and user adjustable atrial and ventricular sensitivities. The dual chamber demand pacing mode, e.ga. the DDD or DDI mode, is in effect as long as the atrial and ventricular pace pulse amplitudes are set by the user within an operative range. The pacing mode is switched to a single chamber demand mode when one of the atrial and ventricular pace pulse energies is set to an inoperative setting which preferably is a no output setting. If the atrial pace pulse amplitude is set to no output, then the mode is switched to a single chamber demand mode with ventricular sensing and pacing, preferably the VVI mode. If the ventricular pace pulse amplitude is set to no output, then the mode is switched to a single chamber mode with atrial sensing and pacing, preferably the AAI mode. In the implementation of the invention, the setting of atrial or ventricular pace pulse amplitude to the OFF position is detected, and the corresponding atrial or ventricular sense amplifier is effectively rendered inoperative, resulting in the mode switch. The mode switch back to the dual chamber demand pacing mode is effected by setting the atrial or ventricular pace pulse amplitude to any level other than the no output position. Preferably, the mode switch is back to the DDD mode, even if the preceding mode switch was from the DDI mode.

29 Claims, 10 Drawing Sheets

OTHER PUBLICATIONS

"Medtronic® Model 5346 Temporary Pacemaker" UC9302111EN, ©Medtronic, Inc. Jul. 1993.

"Medtronic® Model 5346 Temporary Pacemaker", UC9301879aEN, ©Medtronic, Inc. 1994.

"Medtronic 5375 Pulse Generator Technical Manual", Aug. 1990, UC8801618aEN 176599–002.

"External Ventricular Pacemaker Model 5375"UC8901873aEN, ©Medtronic, Inc. 1990, Jun. 1990.

"Pacemakers, Cardiac, External Invasive", published by Healthcare Product Comparison System, 5200 Butler Pike, Plymouth Meeting, PA 19462–1298, U.S.A. Jan. 1996, 185821, 424–008.

"Technical Concept Paper: Benefits of DDD Mode for Temporary Pacing", UC9204388EN, ©Medtronic, Inc. 1993.

| INSTRUCTIONS | | AOO | VOO | AAI | VVI | DOO | DVI | DDD | DDI |
|---|---|---|---|---|---|---|---|---|---|
| | PACE INDICATOR | A | V | A | V | A+V | A+V | A+V | A+V |
| | SENSE INDICATOR | NONE | NONE | A | V | NONE | V | A+V | A+V |
| 1. VERIFY OUTPUT | A OUTPUT | ON | OFF | ON | OFF | ON | ON | ON | ON |
| | V OUTPUT | OFF | ON | OFF | ON | ON | ON | ON | ON |
| 2. VERIFY SENSITIVITY | A SENSITIVITY | ASYNC | NA | ON | NA | ASYNC | ASYNC | ON | ON |
| | V SENSITIVITY | NA | ASYNC | NA | ON | ASYNC | ON | ON | ON |
| 3. VERIFY ATRIAL TRACKING | A TRACKING | NA | NA | NA | NA | NA | NA | ON | OFF |

FIG. 9

| MODE | CONTROL CHANGE | RESULTING MODE |
|---|---|---|
| DDD | Ao ⟹ OFF | VVI |
| | Vo ⟹ OFF | AAI |
| | As ⟹ ASYNC | DVI |
| | Vs ⟹ ASYNC | DAD |
| | ATRIAL TRACKING ⟹ OFF | DDI |
| DAD | Ao ⟹ OFF | VOO |
| | Vo ⟹ OFF | AAI |
| | As ⟹ ASYNC | DOO |
| | Vs ⟹ ON | DDD |
| DVI | Ao ⟹ OFF | VVI |
| | Vo ⟹ OFF | AOO |
| | As ⟹ ON | DDD |
| | Vs ⟹ ASYNC | DOO |
| DDI | Ao ⟹ OFF | VVI |
| | Vo ⟹ OFF | AAI |
| | As ⟹ ASYNC | DVI |
| | Vs ⟹ ASYNC | DAD |
| | ATRACK ⟹ ON | DDD |
| DOO | Ao ⟹ OFF | VOO |
| | Vo ⟹ OFF | AOO |
| | As ⟹ ON | DAD |
| | Vs ⟹ ON | DVI |
| VVI | Ao ⟹ ON | DDD |
| | Vo ⟹ OFF | OOO |
| | Vs ⟹ ASYNC | VOO |
| AAI | Ao ⟹ OFF | OOO |
| | Vo ⟹ ON | DDD |
| | As ⟹ ASYNC | AOO |
| VOO | Ao ⟹ ON | DAD |
| | Vo ⟹ OFF | OOO |
| | Vs ⟹ ON | VVI |
| AOO | Ao ⟹ OFF | OOO |
| | Vo ⟹ ON | DVI |
| | AS ⟹ ON | AAI |
| OOO | Ao ⟹ ON | AAI |
| | Vo ⟹ ON | VVI |

FIG. 10

DUAL CHAMBER, MULTI-MODE EXTERNAL PACEMAKER

CROSS-REFERENCE TO RELATED APPLICATION

Reference is hereby made to commonly assigned, co-pending U.S. patent application Ser. No. 08/544,882 filed on even date herewith for QUICK CHANGE BATTERY DRAWER FOR EXTERNAL ELECTRICAL STIMULATOR in the names of David B. Engmark et al.

BACKGROUND OF THE INVENTION

1. Field of the Invention

The present invention relates to dual chamber cardiac pacemakers having multiple single chamber and dual chamber pacing modes, and more particularly to a method and apparatus for effecting mode switching between selected primary pacing modes.

2. Description of the Background Art

Dual chamber pacing modes have been widely adopted for pacing therapy in both external, bedside pacing systems and implantable pacing systems. Among the dual chamber pacing modes is the "DDD" mode, which can pace the atrium and ventricle, senses both the atrial and ventricular depolarization signals (P-waves and R-waves, respectively), and can either inhibit or trigger pacing stimuli for both chambers. Other dual chamber pacing modes include the DVI pacing mode which can pace the atrium and ventricle, but senses only R-waves, and can either inhibit or trigger ventricular pacing stimuli, and the VDD pacing mode which can pace the ventricle, senses both P-waves and R-waves, and can inhibit ventricular pacing stimuli. These three letter mode codes are standardized in the pacing industry as "NBG" codes published in 1987 by the North American Society of Pacing and Electrophysiology (NASPE) and the British Pacing and Electrophysiology Group (BPEG). The first letter denotes the heart chamber paced, the second letter denotes the chamber sensed and the third letter denotes the function in response to a sensed event. The letters A, V, D, T and I are employed wherein "A" specifies an atrial function, "V" specifies a ventricular function, "D" specifies both A and V functions, "T" means a triggered operation, and "I" means an inhibited operation. The three letter code is expanded by a further letter "R" to signify a mode of operation involving establishing pacing rate in response to a physiologic sensor representing a patient's level of activity or need for cardiac output.

The three letter code is often used (1) to generally characterize a type of pacemaker, (2) to signify a programmed primary pacing mode of a multi-mode, implantable programmable, pacemaker or the manually set, primary pacing mode of a multi-mode, external pacemaker, or (3) to indicate the current pacing mode within the family of possible current pacing modes included inherently within a programmed or set primary pacing mode that largely depends on the behavior of the patient's heart in relation to the adjustable pacing, sensing and rate parameters of the pacemaker pulse generator as described below. In the following description of the background art and the invention, unless otherwise noted, references to the pacing mode are to the primary pacing mode within the family of possible primary pacing modes of what is generally characterized as a DDD dual chamber pacemaker type not having a rate response capability. Moreover, references to "mode switching" made herein are to be distinguished from the term as used in describing the modes of operation attendant to establishing a pacing rate in response to a physiologic sensor rather than in response to an atrial depolarization or a programmed lower pacing rate.

A DDD dual chamber pacemaker in the DDD pacing mode requires a pulse generator having atrial and ventricular pace/sense leads attached thereto. The pulse generator in the DDD pacing mode requires an atrial sense amplifier to detect P-waves conveyed through the atrial pace/sense lead, a ventricular sense amplifier to detect R-waves conveyed through the ventricular pace/sense lead, a timing and control system for establishing pacing modes and time intervals for sensing and pacing operations, and ventricular and atrial output circuits to provide atrial and ventricular pacing pulses to the appropriate lead. If the P-wave is not sensed within a predefined time interval (atrial escape interval), the pacemaker supplies an atrial pacing pulse to the atrium through the atrial pace/sense lead. The atrial escape interval may be characterized in terms of a ventricular-to-atrial (V-A) interval. Following an atrial event (either sensed or paced), the timing and control system establishes an atrial-ventricular (A-V) interval. If the A-V interval lapses before an R-wave is sensed, the pulse generator supplies a ventricular pacing pulse to the ventricle through the ventricular pace/sense lead. The combined V-A and A-V interval that the pacemaker is set to operate at is sometimes referred to as the A—A interval or the V—V interval or the lower rate interval.

Pacemakers operating in the DDD pacing mode have the capability of tracking the patient's natural sinus rhythm and preserving the hemodynamic contribution of the atrial contraction over a wide range of heart rates between the lower rate and an upper rate limit. For this reason, the DDD mode is typically the primary pacing mode of a dual chamber pacing system that is programmed into an implantable pulse generator or manually set for an external pacemaker. The related DVI or VDD modes may be programmed or manually set to be the primary pacing mode if the patient has little or no underlying atrial sinus rhythm or intermittent A-V conduction with intact sinus rhythm.

Such DDD pacing systems are also typically programmable or operable in single chamber pacing modes, typically the AAI and VVI modes, where sensing and pacing are restricted to the atrium and ventricle, respectively. In practice, a very small percentage of implanted DDD pulse generators are programmed into these single chamber modes unless a problem arises with sensing or pacing through the atrial or ventricular lead bearing electrodes.

In external pacemakers typically used during a patient stay in a medical facility, the DDD pacing mode architecture provides the economy and flexibility of being used for either the single chamber or the dual chamber modes. The appropriate temporary lead system may be positioned in the patient, depending on the patient need, and the pulse generator may be switched to operate in one of the modes prescribed by the attending physician. For example, during open heart surgery, removable, temporary atrial and ventricular electrode bearing leads may be attached to the heart for post-operative DDD pacing during the recovery period and until the leads are removed. If one of the electrodes is dislodged from the heart, it may be necessary to switch to the appropriate single chamber pacing mode for the remaining electrode. In other cases, temporary single chamber pacing may be prescribed from the outset. Such typical external pacemaker pulse generators include the Medtronic® Model Nos. 5342, 5345 and 5346 external pacemakers, the Telectronics® Model 4553 external pacemaker, and the Pacesetter Systems, Inc. Model 3070 external pacemaker.

The pacing mode is typically selected in these external pulse generators through the adjustment of a mode setting switch. When the mode is selected, the physician also sets appropriate pacing parameters for the pacing mode. The pacing parameters set include atrial and/or ventricular sense amplifier sensitivities to the P-wave and/or R-wave signal to provide a suitable amplification to disregard background noise and reliably provide true A-sense and/or V-sense trigger signals to the timing and control system. The pacing parameters set also include atrial and/or ventricular pulse generator output pulse amplitudes to provide a suitable safety margin over the capture threshold for the atrium and/or ventricle.

If it becomes necessary to adjust the pacing mode or the parameters due to a change in the patient's condition or dislodgement of a temporary lead, the changes may have to be made by attending staff that are not as familiar with the pacing modes or setting of the sensitivity and pacing amplitude parameters. In addition, in any case, some medical personnel do not understand the NBG code and find the pacing modes difficult to understand. Confusion may occur and the wrong settings may be made. A need exists for a simplified manner of setting the pacing modes and parameters of external DDD pulse generators.

SUMMARY OF THE INVENTION

It is therefore an object of the present invention to provide a simplified operating system for setting the pacing modes and parameters of an external DDD pacemaker pulse generator.

In accordance with the present invention, an external DDD pulse generator having user adjustable atrial and ventricular sensitivities is operated in a dual chamber demand pacing mode, e.g. the DDD or DDI modes, as long as the atrial and ventricular pace pulse amplitudes are set by the user within operative ranges, and the pacemaker is switched to a single chamber demand mode when one of the atrial and ventricular pace pulse amplitudes is set to an inoperative setting which preferably is a no output or OFF setting. If the atrial pace pulse amplitude is set to no output (OFF), then the mode is switched to a further pacing mode with ventricular sensing and pacing, e.g. the VVI mode. Conversely, if the ventricular pace pulse amplitude is set to no output (OFF), then the mode is switched to a further pacing mode with atrial sensing and pacing, e.g. the AAI mode.

In the implementation of the invention, the setting of atrial or ventricular pace pulse amplitude to the OFF position is detected, and the corresponding atrial or ventricular sense amplifier is effectively rendered inoperative, resulting in the mode switch. The mode switch back to the dual chamber demand pacing mode is effected by setting the atrial or ventricular pace pulse amplitude to any level other than the OFF position. Preferably, the mode switch is back to the DDD mode, even if the preceding mode switch was from the DDI mode.

The present invention advantageously provides the ability to quickly change between the key pacing modes of AAI, VVI and DDD/DDI by simply adjusting the atrial and ventricular pace pulse amplitudes between OFF and an output setting. No special knowledge of the pacing modes is needed for medical staff to operate the pulse generator in these safe modes. The user does not have to also effectively render the atrial or ventricular sense amplifiers inoperative to effect the mode change. All that is needed to understand is that when atrial or ventricular pacing is turned off, then the mode is switched to ventricular inhibited or atrial inhibited pacing, respectively.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 9 is a pacing mode set-up chart of the primary pacing modes of the pulse generator of FIG. 1;

FIG. 10 is a table of mode transition rules under which primary mode changes are made;

DETAILED DESCRIPTION OF THE PREFERRED EMBODIMENTS

In the practice of the present invention, the preferred other pacing modes that are switched to from the DDD/DDI pacing modes in response to settings of the atrial or ventricular pace pulse energies to respective no atrial output or no ventricular output settings are the AAI or VVI pacing modes, respectively. Therefore, the apparatus and illustrated operations of the first preferred embodiment are described in reference to FIGS. 1–11 in this context. However, it will be understood that the other pacing modes may include other single or dual chamber pacing modes that are operable with no atrial output setting or the no ventricular output setting, including the VDD pacing mode of the second embodiment as illustrated in FIG. 12. Therefore, it will be further understood during the following description that the apparatus of FIGS. 1 and 2 may be configured to operate in that manner.

Figure 1:
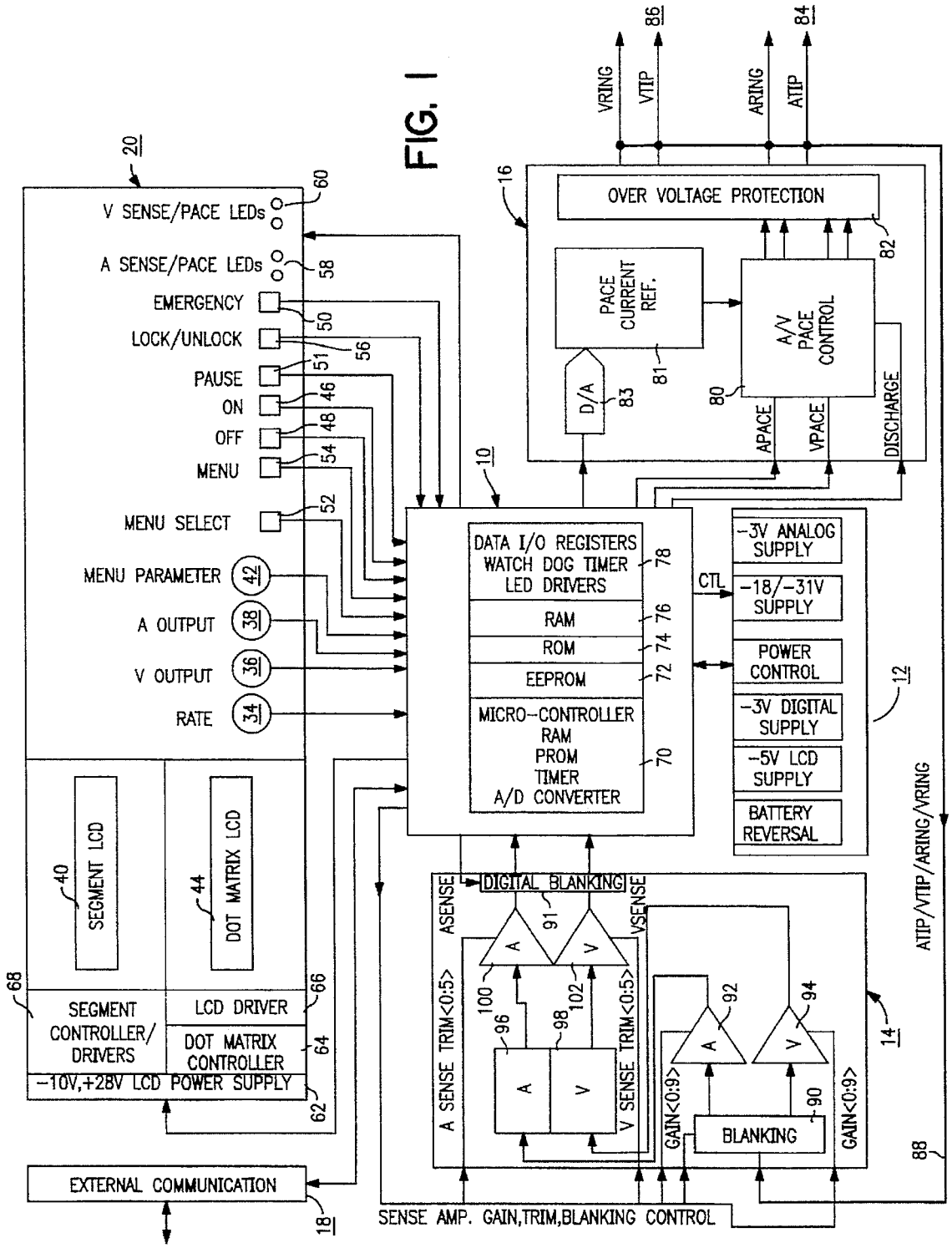
FIG. 1 is a system block level diagram of an external, multi-mode, dual chamber pulse generator with mode and parameter selection and display capable of implementing the mode switching behavior of the present invention.

FIG. 1. depicts the major components of a DDD pulse generator operating system and the mode and parameter selection and display system capable of implementing the simplified mode switching operation of the present invention. The operating system is composed of a timing and control module 10, a power supply module 12, a sense amp module 14, an output module 16, an external communications module 18 and a user interface module 20. The user interface module 20 includes the keys and dials for user input, the LCD display panels and the pace/sense LED displays depicted in the perspective view of the exterior case 30 of FIG. 2 and in FIGS. 4–9.

Figure 2:
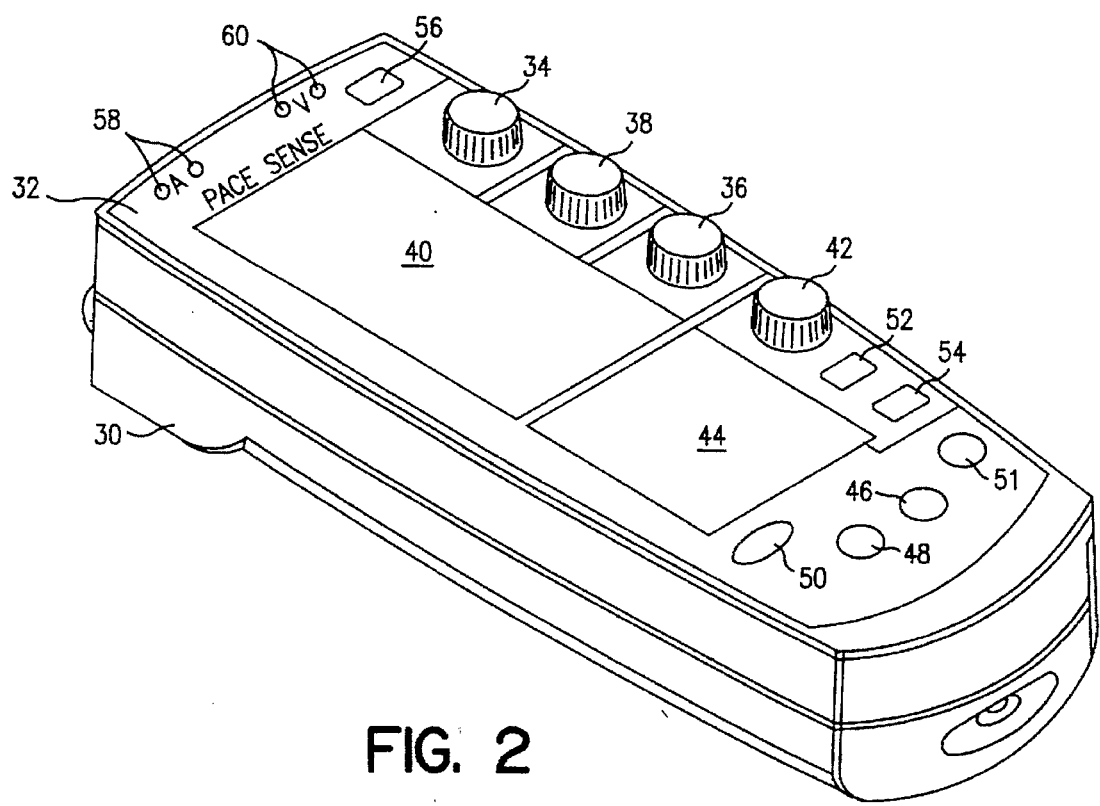
FIG. 2 is a perspective view of the external pacemaker pulse generator of FIG. 1.

The user interface module 20 comprises the face plate 32 of housing 30 through which rotary dials project that provide digitized setting commands to timing and control module 10 as shown in FIG. 2. The rotary dials and their associated operating circuits are preferably 16 position, 2-bit gray code encoders available as Model $388^{EN-4P}$ from Clarostat, Inc. The rotary dials can be rotated clockwise or counterclockwise through an unlimited number of steps with the gray code repeating every four steps in the same direction. Each step change effects a change in the gray code, and the direction of rotation can be readily determined from the change from the previous gray code. The signal processing speed is far greater than the speed at which the dials can be manually rotated, and therefore, the number of step changes can be readily tracked by the code changes.

These rotary dials include the pacing rate dial 34, the V-pace output amplitude dial 36, and the A-pace output amplitude dial 38 which may be manually rotated to settings displayed in segment LCD display panel 40 behind a transparent portion of face plate 32. A further Menu Parameter rotary dial 42 projects through face plate 32 adjacent to the dot matrix LCD display panel 44 behind a further transparent portion of face plate 32 which may be rotated to select a menu of adjustable parameters for the particular pacing mode as described below. Further manually depressible, two position, labelled keys, including the ON key 46, OFF key 48, Emergency key 50, Pause key 51, Select key 52, Menu key 54, and Lock/Unlock key 56, are flush mounted in face plate 32. An atrial sense/pace pair 58 of LEDs and a ventricular pace/sense pair 60 of LEDs also provide displays on the face plate 32 that flash with paced and sensed events.

The Menu key 54 is used to select menus of selectable parameters appropriate to the selected pacing mode that are displayed on the dot matrix LCD display panel 44. As described below, the menus include one or more parameter, including the atrial and ventricular sense amplifier sensitivity settings, which can be selected by depressing the Select key 52 until the desired menu item is highlighted in a scrolling process. When the parameter is selected, it may be adjusted in value by rotation of the Menu Parameter dial 42.

The Emergency key 50 causes a mode switch to the DOO pacing mode at preset maximal A-pace and V-pace output energies. The Pause key 51 is used to inhibit the output pulses. The Lock/Unlock key 56 prevents accidental changes of rate and output parameter settings when in the Lock position and allows changes to be made when in the Unlock position. Adjustment of the pacing rate dial 34 effects the setting of an A-V interval, the upper rate limit for tracking the patient's P-waves, and the post-ventricular atrial refractory period (PVARP) for use in dual chamber pacing modes. Specific details of the menu items will be described below.

The user interface module 20 also includes regulated LCD power supply 62, dot matrix controller 64, LCD driver 66, and segment controller/driver 68 which respond to signals from timing and control module 10 in response to the settings of the above listed dials and keys to display the current pacing mode, the pacing rate in ppm and the atrial and ventricular output energies in mA in the segment LCD display panel 40 and the atrial and/or ventricular sense amplifier sensitivities, the A-V interval the ON/OFF status of atrial tracking and other menu selections in the dot matrix display panel 44.

The timing and control module 10 includes a microcontroller 70, including RAM, PROM, timer and A/D converter, EEPROM 72, ROM 74, RAM 76 and a digital logic block 78 comprising data I/O registers, a discrete "watch dog" timer for setting a fallback pacing rate in case of operating system failure, and LED drivers that respond to trigger signals from micro-controller 70 to cause the atrial and ventricular sense/pace LED pairs 58 and 60 to flash in synchrony with sense and pace events. The power supply module 12 includes a number of regulated voltage and current supply circuits for the digital circuit timing and control module 10 and the analog circuit modules.

The pacing output module 16 includes an A/V pace control circuit 80 including atrial and ventricular pulse generator circuits coupled through over voltage protection circuit 82 to the atrial and ventricular connector terminal pairs 84 and 86, respectively. The atrial connector terminal pair 84, labelled ARING and ATIP, and the ventricular connector terminal pair 86, labelled VRING and VTIP, are adapted to receive and be connected to the connector ends of atrial and ventricular pace/sense leads in a manner well known in the art. The atrial and ventricular pulse generator circuits within A/V pace control circuit 80 operate as constant current devices that apply fixed pulse width, variable amplitude pace pulses to the respective heart chamber. A pace current reference circuit 81 generates the current for the A-pace and V-pace pulse energies in response to a digital signal received by D/A converter 83 from timing and control module 10 in a manner well known in the art. The A-pace and V-pace pulse energies are established by micro-controller 70 from the settings of the A-pace and V-pace output amplitude dials 38 and 36.

The A-pace and V-pace pulses are delivered through the A/V pace control circuit 80 to the heart tissue between the pace/sense electrodes coupled to the atrial and ventricular connector terminal pairs 84 and 86 in the conventional manner in response to APACE and VPACE commands from the timing and control circuit 10. Output capacitors are included in the A/V pace control circuit 80 coupled to the connector terminal pairs 84 and 86 and tend to charge during the delivery of the APACE and VPACE pulse energies. The Discharge signal is provided by micro-controller 70 to discharge the charge accumulated in these capacitors before the next pace pulse is to be delivered.

The atrial connector terminal pair 84 and the ventricular connector terminal pair 86 are also hard wired through individual lines in bus 88 to atrial and ventricular channel inputs of an analog blanking circuit 90 of sense amp module 14. The analog blanking circuit 90 responds, in a manner well known in the pacing art, to blanking interval signals generated by micro-controller 70 following an APACE or VPACE trigger signal to prevent passage of any signal inputted thereto on bus 88 to the input terminal of the atrial or ventricular differential amplifier 92 or 94. Assuming that the blanking signal is absent, signals at the atrial or ventricular connector terminal pairs 84 or 86 are amplified by the respective atrial or ventricular differential amplifier 92 or 94 and applied to the input terminals of band pass filters 96 or 98. The band pass filtered signals are amplified by A-sense and V-sense amplifiers 100 or 102, resulting in ASENSE or VSENSE signals, if the amplified and filtered input signals satisfy detection criteria for distinguishing a P-wave or R-wave from background noise, EMI or other heart signals and artifacts in a manner well known in the art. The ASENSE and VSENSE signals are applied through atrial and ventricular digital blanking channels in digital blanking circuit 91 to data I/O registers within digital logic block 78. The micro-controller 70 responds to the registered ASENSE and VSENSE signals to control the current pacing operation, e.g. to reset the A-V and V-A intervals, in a manner well known in the art.

As described below, A sensitivity and V sensitivity parameters are adjustable by the medical staff depending on the menu selection available in the selected pacing mode over a range of operating values, including values that result in loss of sensing, and in an "ASYNC" position. The micro-controller 70 interprets the sensitivity adjustment, within the operating range, displays the scale setting on the dot matrix LCD display panel 44, and provides the appropriate A-gain signal or V-gain signal to the atrial differential amplifier 92 or the ventricular differential amplifier 94 to adjust the sensitivity.

When the A Sensitivity or V Sensitivity parameter is adjusted to the ASYNC setting, a primary pacing mode switch may be effected as described below. In switching to these modes, which include the AOO, VOO, DOO, DAD and DVI, the appropriate sense amplifier channel in sense amp module 14 is effectively rendered inoperative to provide the ASENSE or VSENSE signal to the data I/O registers within digital logic block 78. This is effected by a sense amp channel disable signal applied to the digital blanking circuit 91 for the particular sense amplifier channel, in a manner well known in the art. Alternative or redundant methods of rendering the sense amp channel inoperative may be effected in software or in the sense amplifier channels, including the analog blanking circuit 90 and/or the gain and trim settings of amplifiers 90, 92 and 100, 102.

The pulse generator modules 10-18 may take the form of any of the known, micro-processor based and software driven multi-mode DDD pulse generator architectures. Timing and control module 10 defines the pacing or escape interval inversely related to the pacing rate adjusted by the user, which may take the form of an A—A escape interval for atrial pacing modes and dual chamber pacing modes initiated on an ASENSE or APACE trigger signal and triggering the next APACE at the expiration thereof in the absence of an ASENSE. In ventricular pacing modes the V—V escape interval, initiated on VSENSE or VPACE trigger signals is timed out to issue the next VPACE trigger signal in the absence of a VSENSE trigger signal. Timing and control module 10 similarly times out A-V delay intervals SAV and PAV that commence following an ASENSE and an APACE trigger signal, respectively. The specific values of the A—A, V—V, SAV and PAV intervals are defined by the values selected by the user.

Timing and control module 10 also defines the above mentioned atrial blanking interval following delivery of an APACE trigger signal, during which atrial sensing is disabled, as well as ventricular blanking intervals following delivery of either an APACE or VPACE trigger signal, during which ventricular sensing is disabled. Timing and control module 10 also defines a total atrial refractory period (TARP), including the AV interval and a post-ventricular atrial refractory period (PVARP), during which atrial sensing is disabled or the ASENSE signal is ignored for the purpose of resetting the escape interval. The TARP extends from the beginning of the SAV or PAV interval following either an ASENSE or APACE trigger signal, and continues a predetermined period of time following sensing of a VSENSE or VPACE trigger. A ventricular refractory period (VRP), which is typically shorter than the portion of the PVARP following ventricular sensing or pacing, is generated after either a VSENSE or a VPACE signal. In the case of a premature ventricular contraction (PVC), both a VRP and a PVARP, defined by the timing and control module 10 separately from the ARP, are generated.

In accordance with the present invention, switching between pacing modes is simplified in a user friendly set of control dials and keys and displays as shown in FIGS. 1 and 2 and mode switching software. In this regard, the micro-controller 70 in timing and control module 10 responds to changes in the settings of the dials and keys which are received as digitized signals from the user interface module 20 on a data bus or discrete input lines illustrated in FIG. 1. The depression of a key is detected as a digitally coded interrupt, and the operating system recognizes the coded interrupt to make an pacing mode or condition change.

A step change in position of the pacing rate rotary dial 34, the V-pace and A-pace output amplitude rotary dials 36 and 38, and the Menu Parameter rotary dial 42 is detected as a two-bit gray code change from the immediately preceding code stored in a data I/O register in digital logic block 78. A clockwise dial change can in this manner be distinguished from a counter-clockwise change and be interpreted and displayed as an increase (clockwise change) or decrease (counter-clockwise change) in the preceding parameter value.

Figure 3:
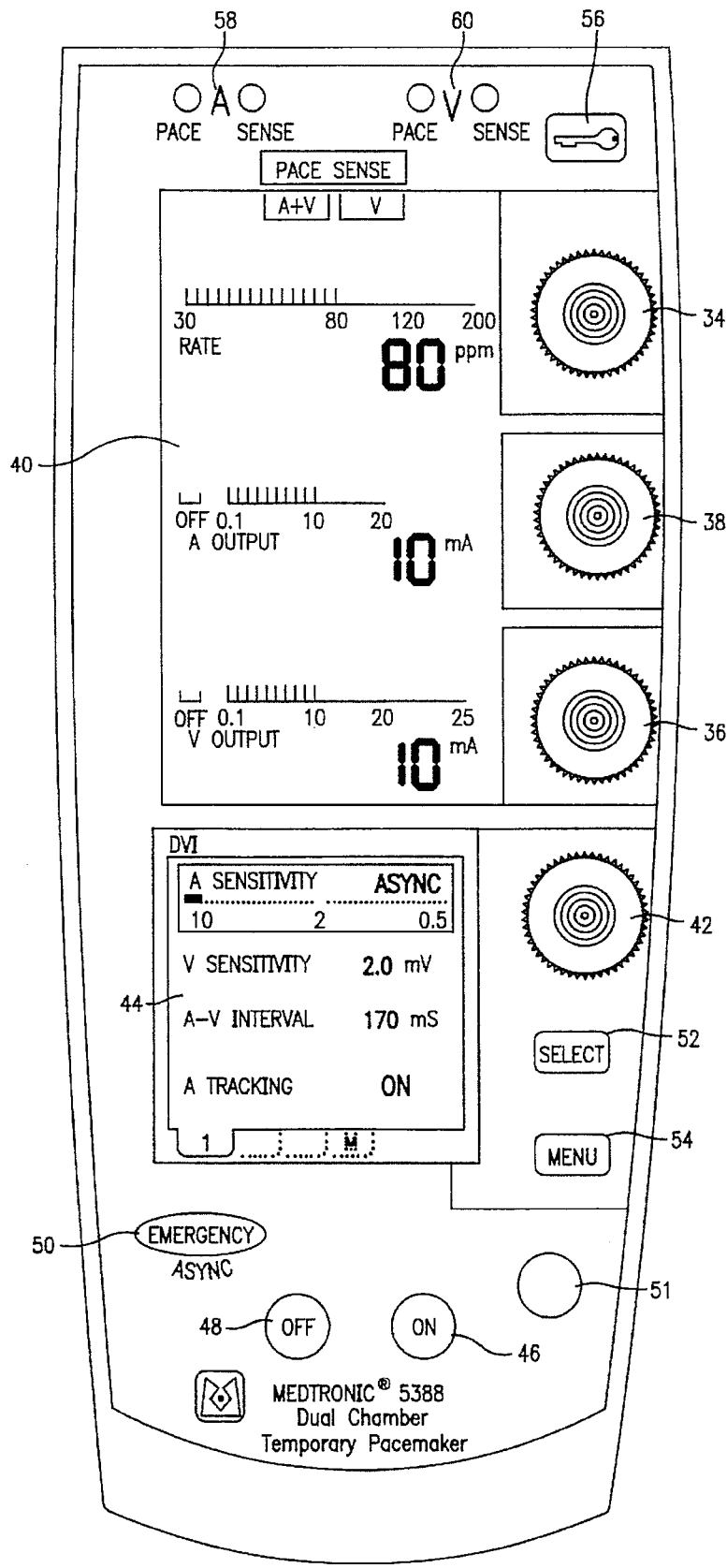
FIG. 3 is a plan view of the face plate and display of the pulse generator of FIGS. 1 and 2 displaying the DDD pacing mode display on start-up and the first menu set of pacing parameters displayed on a dot matrix LCD display panel.

For example, when the ON key is depressed to start-up and turn the system on, the system is initiated to operate in the DDD mode at a preset pacing rate, e.g. 80 ppm, preset A-pace and V-pace output energies, e.g. 10 mA, a preset A Sensitivity, e.g. 0.5 mV, and a preset V Sensitivity, e.g. 2.0 mV, regardless of the current positions of the dials. These settings are depicted in the upper segment LCD display panel 40 of FIG. 3 both numerically and in line/bar graph form. FIG. 3 also depicts the lower dot matrix LCD display panel 44 displaying a first menu set described below. It will be understood that the lower dot matrix LCD display panel 44 is blank on start-up and at all other times unless a menu set is selected as described below.

After start-up, each manual clockwise or counter-clockwise step change in the position of the pacing rate dial 34 or pulse amplitude dials 36, 38 generates a coded interrupt to the micro-controller 70 from which the changed dial can be identified. The micro-controller 70 responds by reading the two-bit data code from the identified dial. The code is compared to the preceding code stored in an I/O register in digital logic block 78, and the change is processed to increase or decrease, respectively, the respective pacing rate or pacing pulse amplitued from the preset value or most recent change from that value.

The Menu items that may be adjusted or set vary with the pacing mode and appear in four sets that are successively displayed by depressing the Menu key 54, individually selected by successively depressing the Select key 52, and adjusted by rotating the Menu Parameter dial 42. The menu items that are not possible to change in the current pacing mode are preferably faintly outlined, while the menu items that can be changed are displayed in bold face. The selected menu item is typically surrounded by a block outline.

The first menu set of pacing parameters, including A Sensitivity, V Sensitivity, A-V Interval, and A Tracking (ON or OFF), are also depicted in FIG. 3 along with the display of the start-up DDD pacing mode. When A Tracking is ON, the dual chamber primary pacing mode is DDD, and when OFF, the dual chamber primary pacing mode is DDI.

Figure 4:
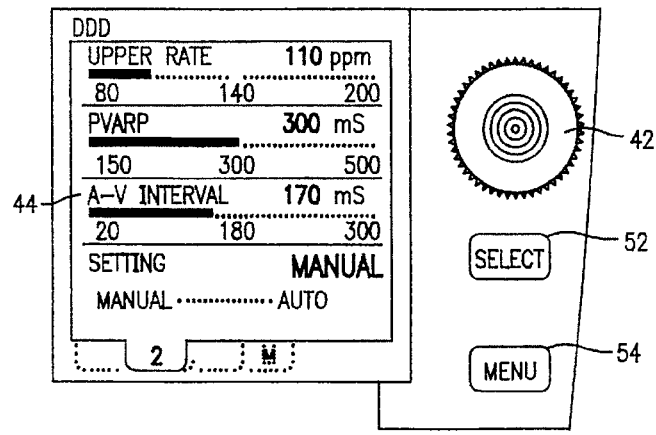
FIG. 4 is a plan view of a selectable second menu set of pacing rate related, pacing parameters displayed on the dot matrix LCD display panel.

A second menu set of dual chamber pacing, lower rate related, pacing parameters, shown in FIG. 4, includes the pacing Upper Rate, PVARP, A-V Interval and a Manual/Automatic function setting. On start-up, the Manual/Automatic function is set to Automatic and the parameter displays show values that are automatically determined from a table as a function of the selected lower pacing rate. In use, when this menu is selected and displayed, the user can then select one of the three parameters and rotate the menu dial to change to a new value from the previous setting, within certain safety limits. The Manual/Automatic function and display is switched to Manual for that parameter, but can be reset to Automatic.

Figure 5:
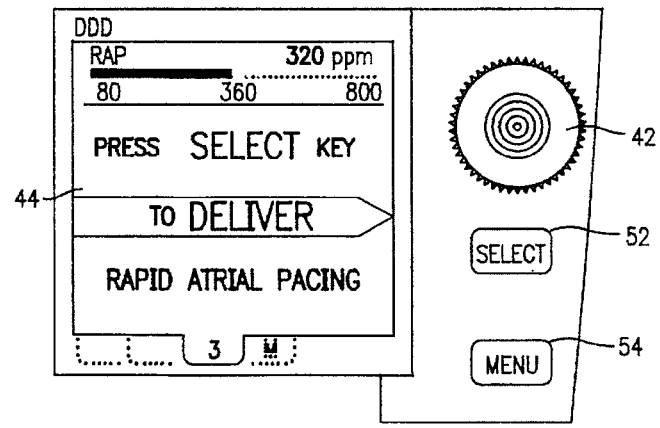
FIG. 5 is a plan view of a selectable third menu set of rapid atrial pacing (RAP) parameters displayed on the dot matrix LCD display panel.
Figure 6:
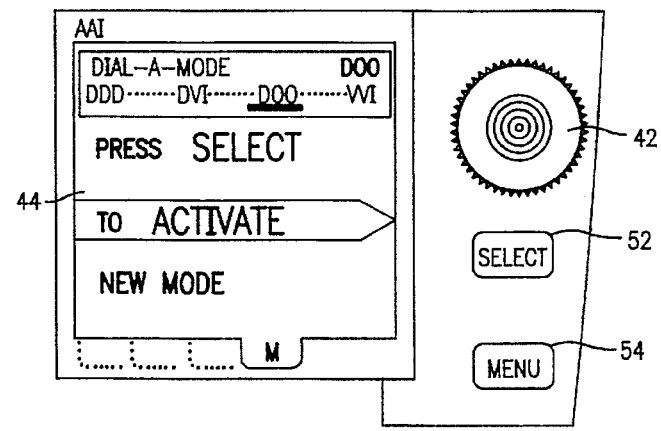
FIG. 6 is a plan view of a selectable fourth menu set of "Dial-A-Mode" selections displayed on the dot matrix LCD display panel.

A third menu set of rapid atrial pacing (RAP) parameters, shown in FIG. 5, include the RAP rate and the Deliver instruction. A fourth menu set of "Dial-A-Mode" selections depicted in FIG. 6 provide for a rapid switch from the displayed current pacing mode (AAI in the depicted example) to possible alternative pacing modes depicted in the upper screen. The display of these menusets of FIGS. 4–8 is blanked if no change is made to a menu item for a certain time, e.g. 60 seconds.

Figure 7:
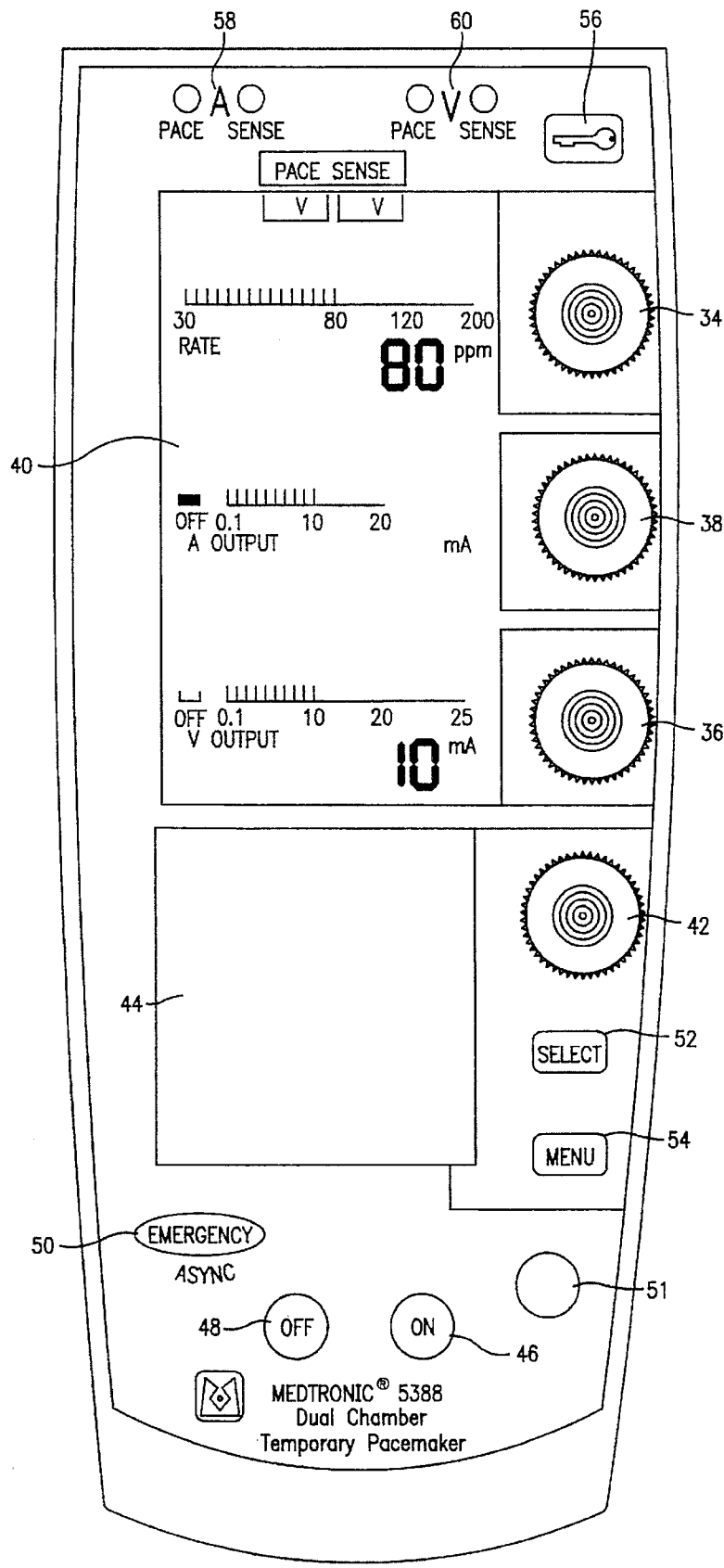
FIG. 7 is a plan view of the segment LCD display panel in the VVI mode upon adjustment of the A-pace output amplitude dial to OFF.
Figure 8:
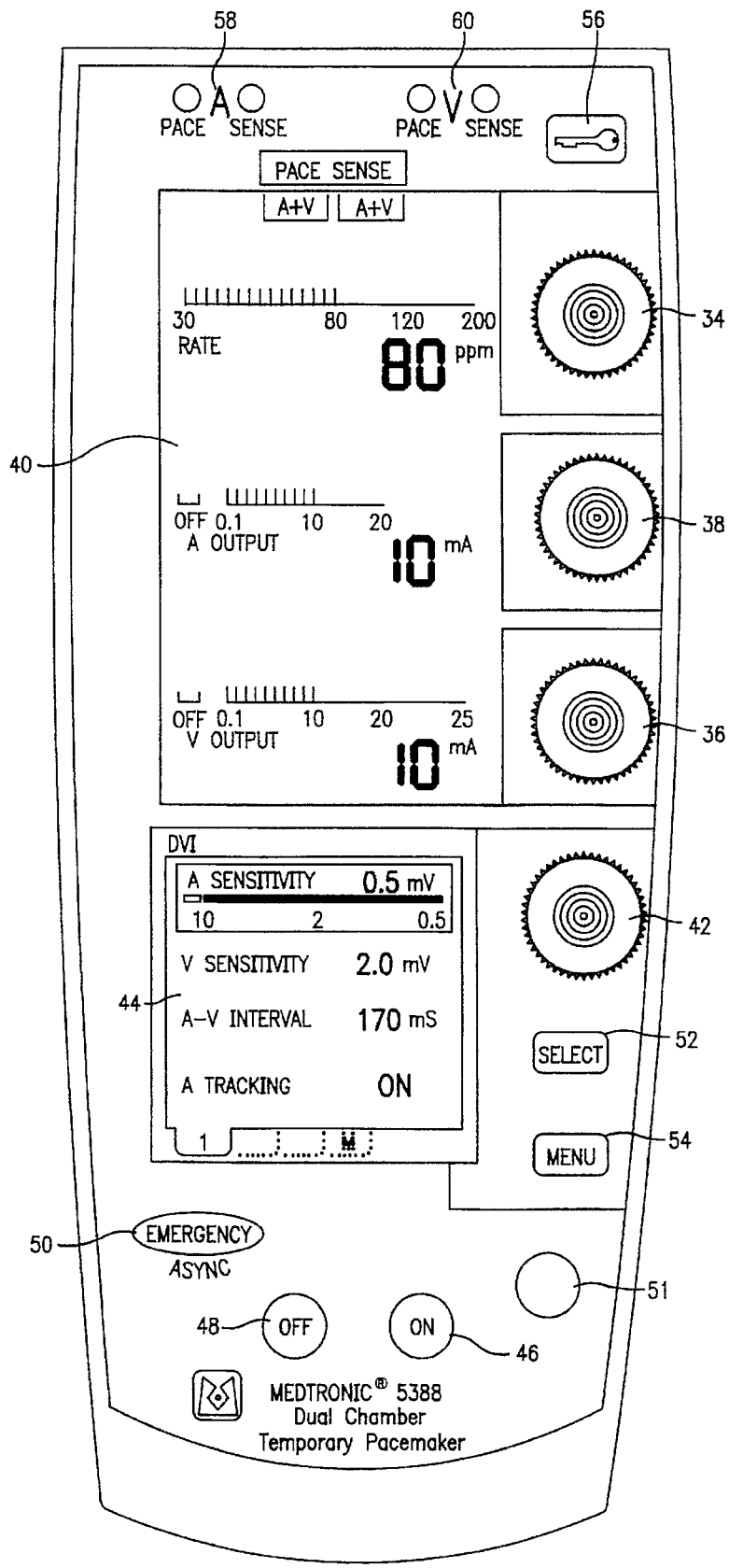
FIG. 8 is a plan view of the segment LCD display panel in the DVI mode upon adjustment of the A Sensitivity to ASYNC.

In accordance with a primary aspect of the present invention, when the V-pace output amplitude dial 36 is stepped counter-clockwise through twenty counted positions from the initial 10.0 mA position depicted in FIG. 3, the V-pace pulse amplitued is displayed as "OFF", and the pacing mode is switched to AAI (as long as an A Sensitivity setting other than ASYNC is maintained). Similarly, when the A-pace output amplitude dial 38 is stepped counter-clockwise through twenty counted positions, the A-pace pacing pulse amplitude is displayed as "OFF", and the pacing mode is switched to VVI (as long as a V Sensitivity setting other than ASYNC is maintained). The segment LCD display panel 40 displays each step change from 10 mV to OFF by a drive signal from micro controller 70. The appearance of the segment LCD display panel 40 in the VVI mode upon adjustment of the A-pace output amplitude dial to OFF is depicted in FIG. 7.

As described above, the dial step changes are detected by micro-controller 70 from the interrupts decoded from the "0" or "1" change in the two-bit gray code, and from a comparison of the current gray code to the preceding stored gray code. The twenty counter-clockwise dial step changes from the 10 mV start-up position, or a lesser number of such step changes from a lower value, are instantaneously detected, and the primary pacing mode switch is made to the AAI or VVI pacing mode.

To fully effect the AAI or VVI mode change, it is also necessary to effectively render the ventricular sense amplifier channel or the atrial sense amplifier channel inoperative. The micro-controller 70 effects this by applying the sense amp disable signal to the respective atrial or ventricular channel in digital blanking circuit 91.

The mode switch back to DDD pacing mode is effected from the AAI mode or the VVI mode by turning the V-pace output amplitude dial 36 or the A-pace output amplitude dial 38, respectively, clockwise and out of the OFF position. All of the nominal DDD parameters are restored and can then be adjusted as considered suitable for the patient.

In this regard, while the primary pacing mode is switched back to the DDD mode with a single dial step change, it should be noted that the atrial or ventricular pace pulse energies may be set too low to capture the heart chamber. The current pacing mode may then exhibit a VDI or ADI behavior within the family of DDD/DDI current pacing modes. Similarly, the atrial or ventricular sense amplifier sensitivity may be set too low, failing to sense respective P-waves or R-waves, and resulting in a mode that could characterized as a DVI or a DAD mode, respectively. These current pacing modes do not constitute mode switches in accordance with the invention.

In accordance with a further subsidiary aspect of the present invention, the ASYNC settings of V Sensitivity and A Sensitivity may also be manually used to effect primary pacing mode switching between less frequently used pacing modes. If both the V sensitivity and the A sensitivity are set to ASYNC and both the V-pace and A-pace output amplitude dials 36 and 38 are adjusted to a level within the 0.1 mA–20.0 mA range, then the primary pacing mode is set to DOO mode. With the A Sensitivity set to ASYNC, adjusting the V-pace output amplitude dial 36 to OFF causes the micro-controller 70 to change the primary pacing mode to AOO mode from the DOO mode (and any of the other modes). If the V-pace output amplitude dial 36 is adjusted back to a level within the 0.1 mA–20.0 mA range, then the primary pacing mode is set to DVI mode. Similarly, the "ASYNC" setting of V Sensitivity concurrently with the OFF setting of A-pace output amplitude dial 38 causes the micro-controller 70 to change the primary pacing mode to VOO mode from the DOO mode and any other pacing mode.

These pacing modes are displayed in the pacing mode setup chart of FIG. 9 in relation to operating instructions followed by the micro-controller 70 in response to an interrupt, including the ON switch interrupt. The table depicts the accessible modes of choice, AOO, VOO, AAI, VVI, DOO, DVI, DDD and DDI, and the pace and sense indicators "A", "V", or "A+V" appearing at the top of the Segment LCD display 40 under "PACE" and "SENSE" inscribed on the face plate 32 when the mode is operative. At each interrupt, the A Output, V Output, A Sensitivity, V Sensitivity, and the A Tracking ON/OFF states and bit values in the I/O registers in digital logic block 78 are polled to verify their settings and states. The new mode is defined by the polled states.

FIG. 10, sets forth the mode transition rules summarizing the above-described mode switching operations that are possible with the pulse generator of FIG. 1. The OOO and DAD modes are accessible but not recommended.

Figure 11:
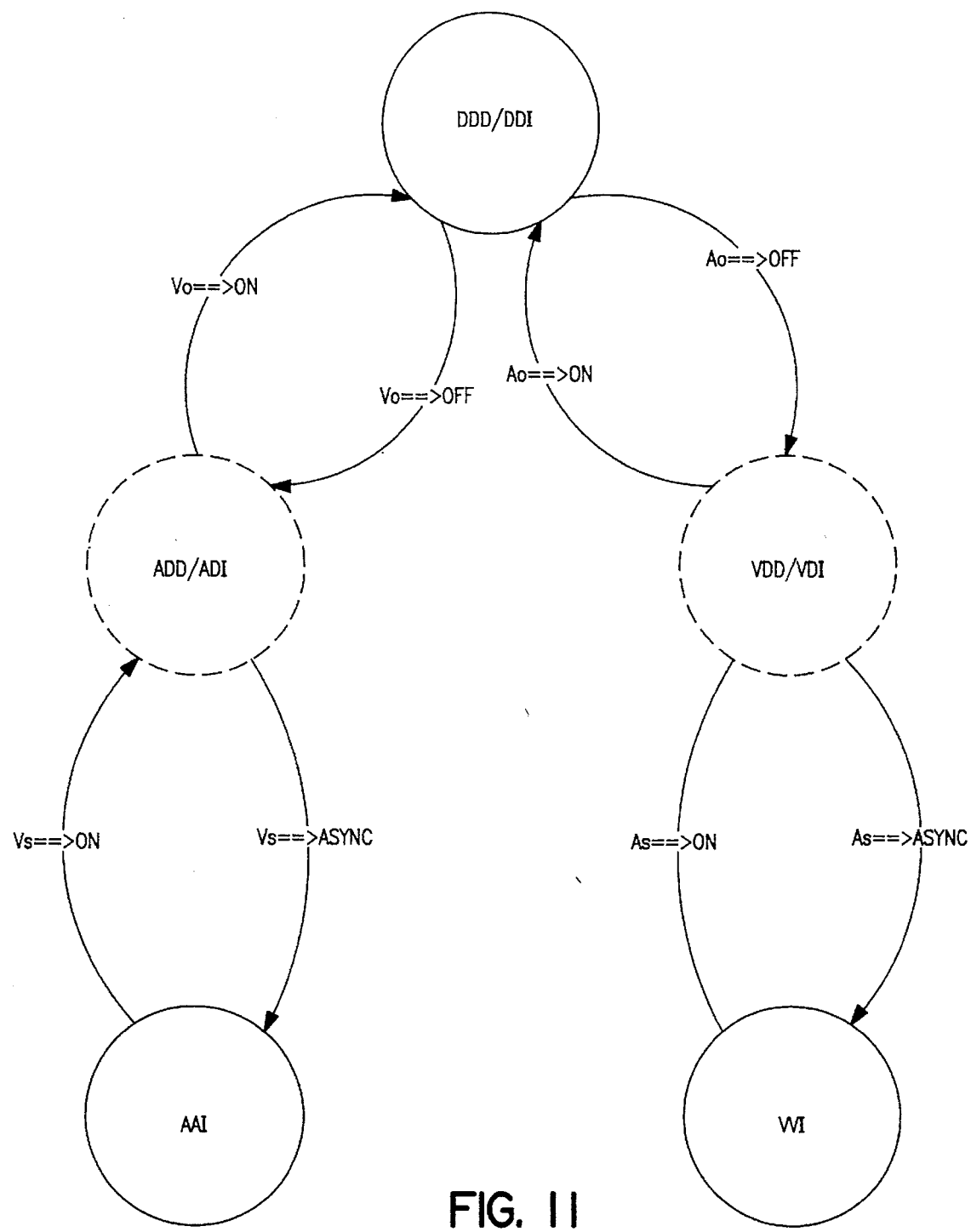
FIG. 11 is a state diagram of the transitions between the DDD/DDI pacing mode and the VVI and AAI pacing modes in accordance with a first embodiment of the invention.
Figure 12:
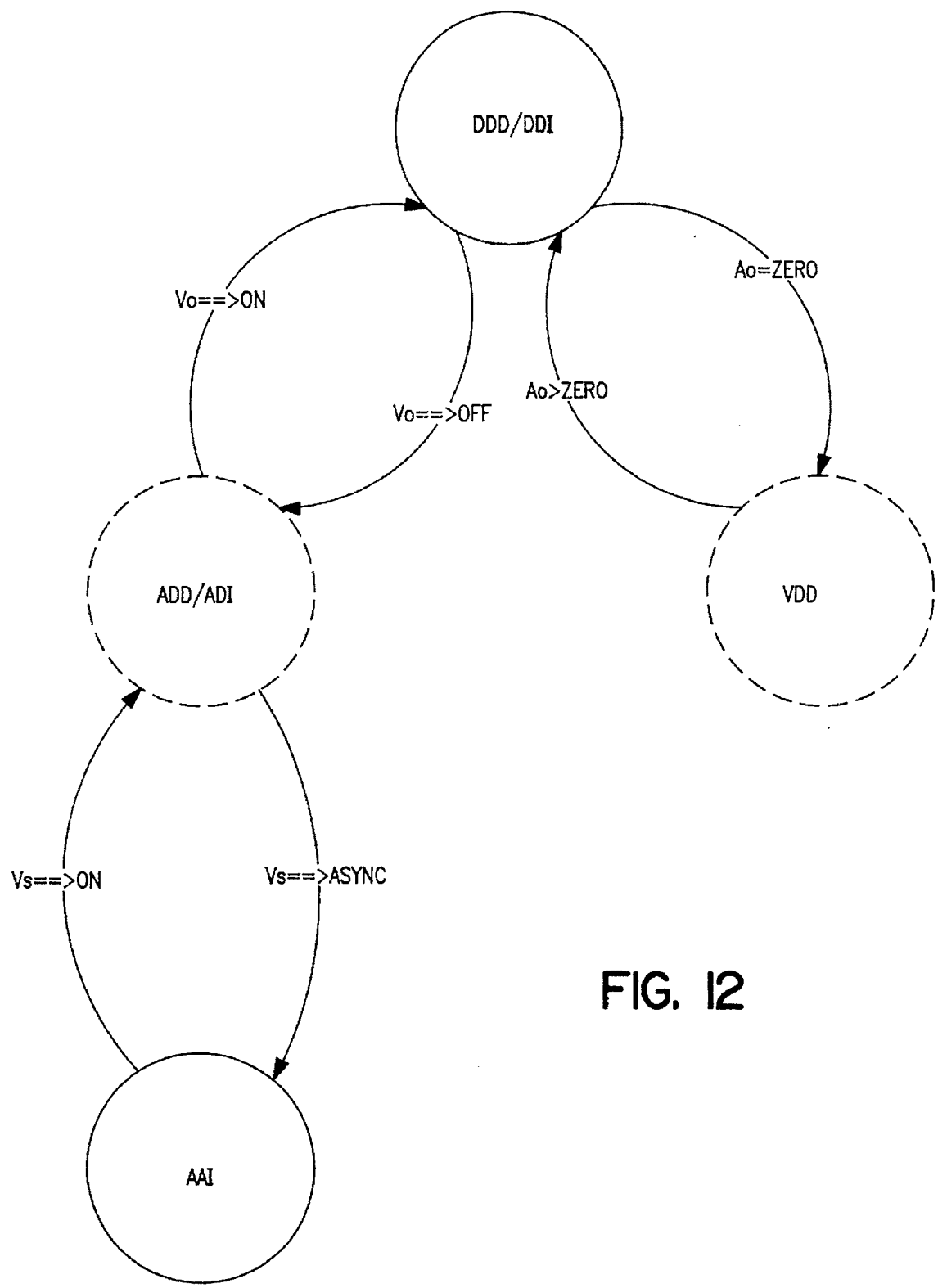
FIG. 12 is a state diagram of the transitions between the DDD/DDI pacing mode and the VDD and AAI pacing modes in accordance with a second embodiment of the invention.

FIG. 11, illustrates the state transitions between the DDD/DDI primary pacing modes and the AAI and VVI pacing modes following the setup and mode change rules of Tables I and II. The imaginary transitional states of VDD/VDI and ADD/ADI are also illustrated to provide a vehicle for illustrating the conditions of the A Sensitivity (As) and V Sensitivity (Vs) that track the setting of A output (Ao) and V output (Vo).

FIG. 12 illustrates the state transitions between the DDD/DDI primary pacing modes and the AAI and an alternative VDD pacing mode. The VDD pacing mode offers certain hemodynamic advantages over the VVI mode in synchronizing the ventricular pace pulse to a sensed P-wave and attendant atrial depolarization, but may not be as readily understandable to the practitioner. The imaginary transitional state of ADD/ADI is also illustrated to provide a vehicle for illustrating the conditions of V Sensitivity (Vs) that track the setting of A output (Ao), as in FIG. 11. The remaining state transitions of the table of FIG. 10 may also be illustrated in the same manner as illustrated in FIGS. 11 and 12.

As stated above, it should understood that the above-described mode switching operations are to be distinguished from forms of mode switching in DDDR pacemaker pulse generators having a rate responsive mode, where pacing rate is established by a physiologic sensor, or an atrial responsive mode, where the pacing rate is dependent on the atrial sinus rate, dependent on the difference between the two rates and an upper atrial tracking rate limit. The present invention may, however, be employed in such a pacing architecture.

The illustrated pulse generator block diagram of FIG. 1 is merely exemplary, and corresponds to the general functional organization of most multi-programmable microprocessor controlled DDD cardiac pacemakers presently commercially available. It is believed that the present invention is most readily practiced in the context of such a device, and that the present invention can therefore readily be practiced using the basic hardware of existing microprocessor controlled dual chamber pacemakers, as presently available, with the invention implemented primarily by means of modifications to the software stored in the PROM and ROM of the timing and control module 10. However, the present invention may also be usefully practiced by means of a full custom integrated circuit, for example, a circuit taking the form of a state machine in which a state counter serves to control an arithmetic logic unit to perform calculations according to a prescribed sequence of counter controlled steps. As such, the present invention should not be understood to be limited to a pacemaker having an architecture as illustrated in FIG. 1, and a circuit architecture as illustrated in FIG. 1 is not believed to be a prerequisite to enjoying the benefits of the present invention.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

Parts List for FIGS. 1–12 timing and control module 10
power supply module 12
sense amp module 14
pacing output module 16
an external communications module 18
user interface module 20
exterior case 30
face plate 32
pacing rate rotary dial 34
V-pace output amplitude rotary dial 36
A-pace output amplitude rotary dial 38
segment LCD display panel 40
menu parameter rotary dial 42
dot matrix LCD display panel 44
ON key 46
OFF key 48
Emergency key 50
Pause key 51
Select key 52
Menu key 54
Lock/Unlock key 56
atrial sense/pace LED pair 58
ventricular pace/sense LED pair 60
regulated LCD power supply 62
dot matrix controller 64
LCD driver 66
segment controller/driver 68
micro-controller 70
EEPROM 72
ROM 74
RAM 76
digital circuit block 78
A/V pace control circuit 80
pace current reference circuit 81
over voltage protection circuit 82
D/A converter 83
atrial connector terminal pair 84
ventricular connector terminal pair 86
bundled cable 88
analog blanking circuit 90
digital blanking circuit 91
atrial differential amplifier 92
ventricular differential amplifier 94
atrial band pass filter 96
ventricular band pass filter 98
A-sense amplifier 100
V-sense amplifier 102

We claim:

1. A multi-mode, dual chamber pacemaker pulse generator adapted to be attached with atrial and ventricular pacing and sensing leads to a patient's heart comprising:

atrial sense amplifier means adapted to be coupled to an atrial pacing and sensing lead for sensing natural atrial depolarizations as atrial sensed events;

ventricular sense amplifier means adapted to be coupled to a ventricular pacing and sensing lead for sensing natural ventricular depolarizations as ventricular sensed events;

atrial pulse generator means adapted to be coupled to said atrial pacing and sensing lead for providing atrial pacing pulses to the patient's atrium at a selected atrial pace pulse amplitude;

atrial pace pulse amplitude adjusting means for adjusting said atrial pace pulse amplitude to amplitude settings in an operating range of delivered atrial pace pulse amplitude and to a no atrial output setting;

ventricular pulse generator means adapted to be coupled to said ventricular pacing and sensing lead for providing ventricular pacing pulses to the patient's ventricle at a selected ventricular pace pulse amplitude;

ventricular pace pulse amplitude adjusting means for adjusting said ventricular pace pulse amplitude to amplitude settings in an operating range of delivered ventricular pace pulse amplitude and to a no ventricular output setting; and timing and control means coupled to said atrial and ventricular sense amplifier means and pulse generator means for responding to atrial and ventricular sensed events for timing intervals and for triggering said atrial and ventricular pulse generators to provide atrial and ventricular pacing pulses in accordance with a pacing mode, said timing and control means including mode switching means for switching the pacing mode of said timing and control means to a dual chamber pacing mode for providing atrial and ventricular pacing and sensing when said atrial and ventricular pace pulse amplitudes are set to said operative ranges and to a further pacing mode when one of said atrial and ventricular pace pulse amplitudes is set to said respective no atrial output and no ventricular output settings.

2. The pacemaker pulse generator of claim 1 wherein said mode switching means is operable to switch the pacing mode of said timing and control means to a single chamber pacing mode.

3. The pacemaker pulse generator of claim 2 wherein said single chamber mode is the AAI pacing mode when said ventricular pace pulse amplitude setting means is set to said no ventricular output setting.

4. The pacemaker pulse generator of claim 2 further comprising:
means for rendering said ventricular sense amplifier means incapable of providing said ventricular sensed event signal to said timing and control means when said ventricular pace pulse amplitude setting means is set to said no ventricular output setting, wherein said single chamber mode is the AAI pacing mode.

5. The pacemaker pulse generator of claim 2 wherein said single chamber mode is the VVI pacing mode when said atrial pace pulse amplitude setting means is set to said no atrial output setting.

6. The pacemaker pulse generator of claim 2 further comprising:
means for rendering said atrial sense amplifier means incapable of providing said atrial sensed event signal to said timing and control means when said atrial pace pulse amplitude setting means is set to said no atrial output setting, wherein said single chamber mode is the VVI pacing mode.

7. The pacemaker pulse generator of claim 1 wherein said mode switching means is operable to set the pacing mode of said timing and control means to the VDD pacing mode when said atrial pace pulse amplitude setting means is set to said no atrial output setting.

8. The pacemaker pulse generator of any one of the claims 1-7 wherein said dual chamber pacing mode is the DDD pacing mode.

9. The pacemaker pulse generator of any one of the claims 1-7 wherein said dual chamber pacing mode is the DDI pacing mode.

10. A simplified method of changing the pacing mode of a dual chamber, rate-responsive pacemaker pulse generator adapted to be attached with atrial and ventricular pacing and sensing leads of the type comprising:
atrial sense amplifier means adapted to be coupled to an atrial pacing and sensing lead for sensing natural atrial depolarizations as atrial sensed events;
ventricular sense amplifier means adapted to be coupled to a ventricular pacing and sensing lead for sensing natural ventricular depolarizations as ventricular sensed events;
atrial pulse generator means adapted to be coupled to said atrial pacing and sensing lead for providing atrial pacing pulses to the patient's atrium at a selected atrial pace pulse amplitude;
atrial pace pulse amplitude adjusting means for adjusting said atrial pace pulse amplitude to amplitude settings in an operating range of delivered atrial pace pulse amplitude and to a no atrial output setting;
ventricular pulse generator means adapted to be coupled to said ventricular pacing and sensing lead for providing ventricular pacing pulses to the patient's ventricle at a selected ventricular pace pulse amplitude;
ventricular pace pulse amplitude adjusting means for adjusting said ventricular pace pulse amplitude to amplitude settings in an operating range of delivered ventricular pace pulse amplitude and to a no ventricular output setting; and
timing and control means coupled to said atrial and ventricular sense amplifier means and pulse generator means for responding to atrial and ventricular sensed events for timing intervals and for triggering said atrial and ventricular pulse generators to provide atrial and ventricular pacing pulses having pulse amplitudes in the adjusted operating ranges thereof, and wherein said method comprises the steps of:
switching the pacing mode of said timing and control means to a dual chamber pacing mode when said atrial and ventricular pace pulse amplitudes are set to said operative ranges;
switching the pacing mode of said timing and control means to an atrial pacing mode when said ventricular pace pulse amplitued setting means is set to said no ventricular output setting; and
switching the pacing mode of said timing and control means to a ventricular pacing mode when said atrial pace pulse amplitude setting means is set to said no atrial output setting.

11. The method of claim 10 wherein said atrial pacing mode is the AAI pacing mode.

12. The method of claim 10 further comprising the step of:
rendering said ventricular sense amplifier means incapable of providing said ventricular sensed event signal to said timing and control means when said ventricular pace pulse amplitude setting means is set to said no ventricular output setting, wherein said single chamber pacing mode is the AAI pacing mode.

13. The method of claim 10 wherein said single chamber pacing mode is the VVI pacing mode when said atrial pace pulse amplitued setting means is set to said no atrial output setting.

14. The method of claim 10 further comprising the step of:
rendering said atrial sense amplifier means incapable of providing said atrial sensed event signal to said timing and control means when said atrial pace pulse amplitude setting means is set to said no atrial output setting, wherein said single chamber pacing mode is the VVI pacing mode.

15. The method of claim 10 wherein said mode switching means is operable to set the pacing mode of said timing and control means to the VDD pacing mode when said atrial pace pulse amplitude setting means is set to said no atrial output setting.

16. The method of any one of the claims 10-15 wherein said dual chamber pacing mode is the DDD pacing mode.

17. The method of any one of the claims 10-15 wherein said dual chamber pacing mode is the DDI pacing mode.

18. A multi-mode, dual chamber pacemaker pulse generator operable in at least the DDD, VVI and AAI pacing and sensing modes, comprising:
atrial sense amplifier means coupled to an atrial pacing and sensing lead for sensing natural atrial depolarizations as atrial sensed events;
ventricular sense amplifier means coupled to a ventricular pacing and sensing lead for sensing natural ventricular depolarizations as ventricular sensed events;
atrial pulse generator means coupled to the atrial lead for providing atrial pacing pulses to the atrium at a selected atrial pace pulse amplitude;
atrial pace pulse amplitude selection means adjustable to one of an operative range setting and a no atrial output setting;

ventricular pulse generator means coupled to the ventricular lead for providing ventricular pacing pulses to the ventricle at a selected ventricular pace pulse amplitude;

ventricular pace pulse amplitude selection means adjustable to one of an operative range ventricular pace pulse amplitude setting and a no ventricular output setting; and timing and control means, coupled to the atrial and ventricular sense amplifier and pulse generator means, for triggering the pulse generators to provide pacing pulses in accordance with the pacing and sensing modes, and having first means for switching the pacing and sensing mode to:

(i) the DDD or DDI mode when the atrial or ventricular pace pulse amplitude selection means is adjusted to the operative range amplitude setting;

(ii) the VVI mode when the atrial pace pulse amplitude selection means is adjusted to the no atrial output setting, and (iii) the AAI mode when the ventricular pace pulse amplitude selection means is adjusted to the no ventricular output setting.

19. The pacemaker pulse generator of claim 18, wherein the switching means further includes second means for switching the pacing and sensing mode from at least one of:

(a) the VVI mode to the DDD or DDI mode when the atrial pace pulse amplitude selection means is adjusted to the operative range amplitude setting, and (b) the AAI mode to the DDD or DDI mode when the ventricular pace pulse amplitude selection means is adjusted to the ventricular operative range amplitude setting.

20. An external multi-mode, dual chamber pacemaker pulse generator operable in at least the DDD and AAI pacing and sensing modes, comprising:

(a) ventricular pulse generator amplitude controlling means adjustable to at least one of an operable range setting where the pulse generator delivers pacing pulses to the ventricle through a ventricular pacing and sensing lead and a no ventricular output setting where the pulse generator delivers no pacing pulses to the ventricle;

(a) timing and control means, coupled to atrial and ventricular sense amplifier and pulse generator means, for providing pacing pulses according to at least the DDD and AAI pacing and sensing modes;

(b) mode switching means, connected to the timing and control means, for switching the pacing and sensing mode to:

(i) the DDD or DDI mode when the atrial or ventricular pace pulse amplitude is adjusted to the operative range amplitude setting, and (ii) the AAI mode when the ventricular pace pulse amplitude is adjusted to the no ventricular output setting.

21. An external multi-mode, dual chamber pacemaker pulse generator operable in at least the DDD and VVI pacing and sensing modes, comprising:

(a) atrial pulse generator amplitude controlling means adjustable to at least one of an operable range setting where the pulse generator delivers pacing pulses to the atrium through an atrial pacing and sensing lead and a no atrial output setting where the pulse generator delivers no pacing pulses to the atrium;

(a) timing and control means, coupled to atrial and ventricular sense amplifier and pulse generator means, for providing pacing pulses according to at least the DDD and VVI pacing and sensing modes;

(b) mode switching means, connected to the timing and control means, for switching the pacing and sensing mode to:

the DDD or DDI mode when the atrial or ventricular pace pulse amplitude is adjusted to the operative range amplitude setting, and (ii) the VVI mode when the atrial pace pulse amplitude is adjusted to the no atrial output setting.

22. An external multi-mode, dual chamber pacemaker pulse generator operable in at least the DDD and AAI pacing and sensing modes, comprising:

(a) ventricular pulse generator amplitude controlling means adjustable to at least one of an operable range setting where the pulse generator delivers pacing pulses to the ventricle through a ventricular pacing and sensing lead and a no ventricular output setting where the pulse generator delivers no pacing pulses to the ventricle;

(b) mode switching means, responsive to the ventricular pulse generator amplitude controlling means, for switching the pacing and sensing mode of the pacemaker to:

(i) the DDD or DDI mode when the ventricular pace pulse amplitude is adjusted to the operable range setting, and (ii) the AAI mode when the ventricular pace pulse amplitude is adjusted to the no ventricular output setting.

23. An external multi-mode, dual chamber pacemaker pulse generator operable in at least the DDD and VVI pacing and sensing modes, comprising:

(a) atrial pulse generator amplitude controlling means adjustable to at least one of an operable range setting where the pulse generator delivers pacing pulses to the atrium through an atrial pacing and sensing lead and a no atrial output setting where the pulse generator delivers no pacing pulses to the atrium;

(b) mode switching means, responsive to the atrial pulse generator amplitude controlling means, for switching the pacing and sensing mode of the pacemaker to:

(i) the DDD or DDI mode when the atrial pace pulse amplitude is adjusted to the operable range setting, and the VVI mode when the atrial pace pulse amplitude is adjusted to the no atrial output setting.

24. A method of switching the pacing and sensing modes of an external, multi-mode, dual chamber pacemaker pulse generator operable in at least the DDD and AAI pacing and sensing modes, wherein the pulse generator comprises: (i) ventricular pulse generator amplitude controlling means adjustable to at least one of an operable range setting where the pulse generator delivers pacing pulses to the ventricle through a ventricular pacing and sensing lead and a no ventricular output setting where the pulse generator delivers no pacing pulses to the ventricle, and (ii) mode switching means, responsive to the ventricular pulse generator amplitude controlling means, for switching the pacing and sensing mode of the pacemaker, the method comprising the steps of:

(a) switching the pulse generator to the DDD or DDI mode when the ventricular pace pulse amplitude is adjusted to the operable range setting, and (b) switching the pulse generator to the AAI mode when the ventricular pace pulse amplitude is adjusted to the no ventricular output setting.

25. A method of switching the pacing and sensing modes of an external, multi-mode, dual chamber pacemaker pulse generator operable in at least the DDD and VVI pacing and sensing modes, wherein the pulse generator comprises: (i) atrial pulse generator amplitude controlling means manually adjustable to at least one of an operable range setting where the pulse generator delivers pacing pulses to the atrium through an atrial pacing and sensing lead and a no atrial output setting where the pulse generator delivers no pacing pulses to the atrium, and (ii) mode switching means, responsive to the atrial pulse generator amplitude controlling means, for switching the pacing and sensing mode of the pacemaker, the method comprising the steps of:

(a) switching the pulse generator to the DDD or DDI mode when the atrial pace pulse amplitude is adjusted to the operable range setting, and (b) switching the pulse generator to the VVI mode when the atrial pace pulse amplitude is adjusted to the no atrial output setting.

26. An external cardiac pacemaker operable in first and second pacing modes, the first pacing mode having first and second operating functions that are disabled when the pacemaker is operating in the second mode, comprising;

adjustable means for selecting an operative characteristic of the first operating function over a pre-defined range of values when the pacemaker is operating in the first mode, and means, responsive to adjustment of the selecting means to an operative characteristic value outside the pre-defined range of values when the pacemaker is operating in the first mode, for disabling the first and second operating functions.

27. An external cardiac pacemaker operable in first and second pacing modes, the first pacing mode having first and second operating functions that are disabled when the pacemaker is operating in the second mode, comprising;

adjustable means for selecting an operative characteristic of the first operating function over a pre-defined range of values when the pacemaker is operating in the first mode, and means, responsive to adjustment of the selection means to an operative characteristic value within the pre-defined range of values when the pacemaker is operating in the second mode, for enabling the first and second operating functions.

28. An external cardiac pacemaker operable in first and second pacing modes, the first pacing mode having a first operating function that is disabled in the second mode, comprising;

adjustable means for selecting an operative characteristic of a second operating function over a pre-defined range of values when the pacemaker is operating in the first mode, and means, responsive to adjustment of the selection means to an operative characteristic value outside the pre-defined range of values when the pacemaker is operating in the first mode, for disabling the first operating function.

29. An external cardiac pacemaker operable in first and second pacing modes, the first pacing mode having a first operating function that is disabled in the second mode, comprising;

adjustable means for selecting an operative characteristic of a second operating function over a pre-defined range of values when the pacemaker is operating in the first mode, and means, responsive to adjustment of the selection means to an operative characteristic value inside the pre-defined range of values when the pacemaker is operating in the second mode, for enabling the first operating function.

* * * * *

UNITED STATES PATENT AND TRADEMARK OFFICE
CERTIFICATE OF CORRECTION

PATENT NO. : 5,626,621
DATED : May 6, 1997
INVENTOR(S) : Richard A. Skogland

It is certified that error appears in the above-identified patent and that said Letters Patent is hereby corrected as shown below:

| | |
|---|---|
| Abstract L. 6 | "e.ga." to be changed to "e.g." |
| C. 7 L. 29 | "and DVI," to be changed to "and DVI modes," |
| C. 8 L. 6 | "VPACE trigger." to be changed to "VPACE trigger signal." |
| C. 14 L. 35 | "amplitued" to be changed to "amplitude" |
| C. 16 L. 6 | "the DDD" to be changed to "(i) the DDD" |
| C. 16 L. 45 | "the VVI" to be changed to "(ii) the VVI" |
| C. 8 L. 57 | "amplitued" to be changed to "amplitude" |
| C. 9 L. 33 | "amplitued" to be changed to "amplitude" |
| C. 14 L. 17 | "amplitued" to be changed to "amplitude" |

Signed and Sealed this

Second Day of May, 2000

*Attest:*

Q. TODD DICKINSON

*Attesting Officer*     *Director of Patents and Trademarks*